(12) United States Patent
Yatsui et al.

(10) Patent No.: US 6,728,568 B1
(45) Date of Patent: Apr. 27, 2004

(54) MAGNETIC RESONANCE IMAGING METHOD AND DEVICE

(75) Inventors: Yumiko Yatsui, Abiko (JP); Tetsuhiko Takahashi, Soka (JP)

(73) Assignee: Hitachi Medical Corporation, Tokyo (JP)

(*) Notice: Subject to any disclaimer, the term of this patent is extended or adjusted under 35 U.S.C. 154(b) by 0 days.

(21) Appl. No.: 09/980,433

(22) PCT Filed: May 26, 2000

(86) PCT No.: PCT/JP00/03385
§ 371 (c)(1),
(2), (4) Date: May 10, 2002

(87) PCT Pub. No.: WO00/72753
PCT Pub. Date: Dec. 7, 2000

(30) Foreign Application Priority Data

May 31, 1999 (JP) .................................. 11-151982

(51) Int. Cl.$^7$ ................................................ A61B 5/055
(52) U.S. Cl. .................... 600/410; 324/307; 324/309
(58) Field of Search ........................ 600/410, 421; 324/307, 309, 312, 322

(56) References Cited

U.S. PATENT DOCUMENTS

| | | |
|---|---|---|
| 5,151,656 A | 9/1992 | Maier et al. |
| RE35,656 E * | 11/1997 | Feinberg et al. ............. 324/309 |
| 6,172,502 B1 * | 1/2001 | Groen et al. ................. 324/307 |
| 6,512,372 B1 * | 1/2003 | Ikezaki ........................ 324/312 |

FOREIGN PATENT DOCUMENTS

JP      568674      3/1993

OTHER PUBLICATIONS

"Phase Error Corrected Interlaced Echo Planar Imaging"; Z. H Cho and C. B Ahn et al.; Proceedings of Annual Meetings of the Society of Magnetic Resonance in Medicine (=SMRM), p. 912 (1987).

"Phase Error in Multi–Shot Echo Planar Imaging"; David A. Feinberg and Koichi Oshio: Magnetic Resonance in Medicine, vol. 32, pp. 535–539 (1994).

* cited by examiner

*Primary Examiner*—Eleni Mantis Mercader
(74) *Attorney, Agent, or Firm*—Cooper & Dunham LLP

(57) ABSTRACT

In order to improve image quality in MRI using an EPI method without extending imaging time excessively, reference data is acquired in the absence of substantial phase encoding gradients by using an EPI sequence in combination with an echo shift (ETS) method, at times related to the timing of echo signals for image data. The reference data is used for phase correcting the image data acquired with application of phase encoding. The reference data can be measured for a single shot, or a few shots, and used to estimate reference data for the rest of the shots in which imaging data is acquired.

15 Claims, 7 Drawing Sheets

MAGNETIC RESONANCE IMAGING METHOD AND DEVICE

FIELD OF THE INVENTION

The present invention relates to magnetic resonance imaging (MRI) method and apparatus, particularly to techniques for removing artifacts in ultra fast MR imaging methods.

BACKGROUND OF THE ART

MRI devices measure spatial distributions of proton density within an object to be examined and spatial distributions of relaxation times from excited states, and form images from measured data. In this manner, MRI devices reveal anatomical and physiological information regarding the human body, head, retroperitoneum, or the like, and create two-dimensional or three-dimensional images for display.

MRI imaging involves applying phase encoded gradient magnetic fields to nuclear spins excited by radio frequency magnetic fields to generate echo signals. The phase encode levels usually are 128, 256, 512 or the like per image. Each echo signal usually is sampled at 128, 256, 512, or 1,024 sampling points, during the application of readout gradient magnetic fields. Two-dimensional Fourier transformation is performed on the measured data to create or reconstruct MR images of, e.g., 256×256 pixels each.

An EPI (Echo Planar Imaging) method has been used as a high-speed imaging method for MRI. In image data derived by the EPI method, a phase errors can be introduced that causes artifacts. The main sources of such phase error in image data from the EPI method include non-uniformities in the MRI static magnetic field and eddy currents caused by the inversion of gradient magnetic field.

An ETS (echo time shifting) technique has been developed to reduce artifacts caused by phase error due to non-uniformities in the static magnetic field. The ETS method is described in publications such as "Phase Error Corrected Interlaced Echo Planar Imaging"; Z. H Cho and C. B Ahn et. al.; Proceedings of Annual Meetings of the Society of Magnetic Resonance in Medicine (=SMRM), No.912, 1987, and "Phase Error in Multi-Shot Echo Planar Imaging"; David A. Feinberg and Koichi Oshio: Magnetic Resonance in Medicine, Vol.32, 535–539 (1994), etc. These publications pertain to configuring pulse sequences in data acquisition. Techniques also have been proposed for reducing artifacts due to both non-uniformities in the static magnetic field and eddy currents generated by inversion of polarity of gradient magnetic fields. Such techniques seek to compensate phase values of image data by reference data being acquired to detect turbulence of phase of echo signals. See, for example, Japanese Patent Laid-Open No. Heisei 5-68674.

Conventionally, in the case of MR imaging performed by an EPI method pulse sequence, the ETS method or the phase correction method are used independently. Each method can reduce artifacts significantly but not remove them completely. If the two methods are combined, it could be thought that the beneficial effect would increase, but corrections performed on data acquired by the ETS method through using reference data may not actually improve image quality, rather it can make an artifact be seen more clearly.

The inventors herein have found a solution that involves acquiring the data in an ETS method at different data acquisition timing for each shot, thereby making the phase of signals different for different shots.

Even if correction is performed by a single set of reference data, the correction may not be performed precisely; accordingly image quality may suffer.

The object of the present invention is to improve image quality of MR images acquired by an EPI method.

Another object of the present invention is to provide magnetic resonance imaging method and MRI apparatus capable of acquiring a good MR image by combining an ETS method and a phase correction method.

DISCLOSURE OF THE INVENTION

In order to solve such problems in this invention, an ETS method and a phase correction method using a plurality of sets of reference data corresponding to a plurality of shots, are combined and performed.

In addition, although the overall imaging time including acquisition of both an image data set and a reference data set may be longer theoretically than when acquiring only an image data set, this invention also discloses an improvement directed to this problem. That is, in order to improve time efficiency by shortening the overall imaging time, reference data is acquired in only one shot, time development of phase error is estimated from the reference data acquired in said one shot, the phase of reference data to all shots is estimated, and phase correction for the entire image data set is thus enabled.

In one embodiment, the present invention comprises a magnetic resonance imaging apparatus having an RF excitation pulse generator, static magnetic field generating means, gradient magnetic field generating coils, high frequency echo detecting coil, and control means for controlling the acquisition of image data from a series of RF echo signals. The echo signals are acquired in respective shots in repetition time periods TR. In each shot, a repetition time TR includes an RF excitation pulse and repeated application of an alternating polarity readout gradient magnetic field. The control means controls the time interval between application of the excitation pulse and the start of the repeated inversions of polarity. Image data acquired with the application of phase encoding gradient magnetic fields is phase corrected by using reference data acquired without phase encoding gradient magnetic fields, or at least substantially without such fields.

The phase correction can involve correcting Fourier transformed image data by using phase information from Fourier transformed reference data, and can involve one-dimensional Fourier transformation of each of said reference data and said image data in the readout direction.

Phase correction can be performed by subtracting phase information of Fourier transformed reference data from phase information of Fourier transformed image data.

The reference data can be derived from actual measurement for a certain time interval; for other time intervals can it be derived from calculations based on the actually measured reference data.

Phase information can be obtained from the transformed reference data resulting from a one-dimensional Fourier transformation of the reference data measured in a readout direction.

Phase change information can also be obtained by calculating phase changes corresponding to difference of time intervals between application of RF excitation pulses and the start of application of gradient magnetic fields with inversion of polarity by using time development of phase distortion estimated from phase information of said transformed reference data.

Time development of phase distortion can be estimated by linear approximation or interpolation.

Estimates of time development of phase distortion can be derived by inter polation or extra polation from phase differences between echoes acquired over a period of time.

Another embodiment of the invention comprises a magnetic resonance imaging method including the steps of (1) applying an RF excitation pulse, and (2) acquiring data by detecting a series of echo signals for readout gradient magnetic field pulses of alternating polarity. The time interval between step (1) and the start of step (2) can vary for different shots. Phase correction can be applied to image data acquired with phase encoding gradient magnetic fields by using reference data obtained without use of substantial (or any) encoding gradient magnetic fields.

Image quality is improved by using an ETS method in combination with a phase correction method, using reference data corresponding to plural shots. Such improvement can exceed the improvement resulting from using either method independently. In addition, imaging time can be shortened by acquiring reference data with only one shot (or few shots) and estimating other reference data, as compared to the time taken for actually measuring reference data for all or a greater number of shots corresponding to the shots for image data.

THE BEST MODE FOR CARRYING OUT THE INVENTION

Figure 3:
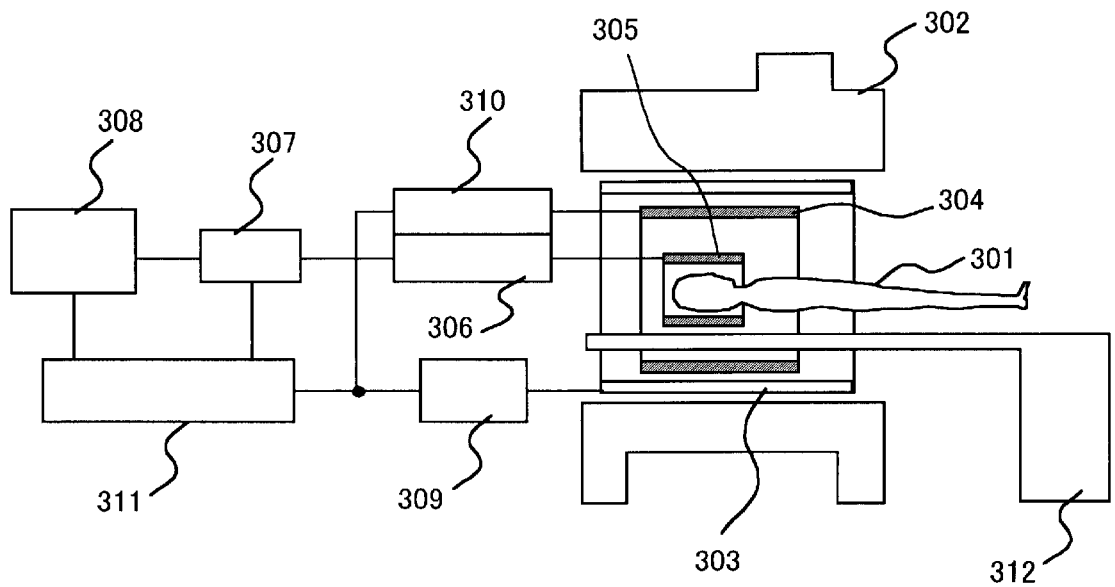
FIG. 3 is a block diagram of an MRI apparatus to which the present invention can be applied.

FIG. 3 is a diagram that shows one example of an MRI apparatus embodying an example of the present invention. In FIG. 3, 302 is a magnet that generates a static magnetic field within a space for an object 301, e.g., a patient. 303 refers to gradient magnetic field coils that generate gradient magnetic fields in the space for object 301. 304 is an RF coil that irradiates a radio frequency magnetic field in said space. 305 is an RF probe that detects NMR signals generated by said object 301. Gradient magnetic field coils 303 comprise a respective gradient magnetic field coil for each of 3 directions —X, Y, Z. These directions are for a slice selection gradient magnetic field coil, a phase encoding gradient magnetic field coil, and a readout direction gradient magnetic field coil. Each coil generates gradient magnetic fields corresponding to signals supplied to each coil from a gradient magnetic field power source 309 for driving each coil. RF coil 304 generates radio frequency magnetic fields corresponding to signals supplied by RF transmitting unit 310. Signals received by RF probe 305 are detected by a signal detection unit 306, the detected signals are processed by a signal processing unit 307, and the processed signals are converted to image data by suitable calculations. The image data is displayed as an image at display unit 308. Gradient magnetic field power source 309, RF transmitting unit 310, and signal detection unit 306 are controlled by software stored in a control unit 311. Usually, the timing sequence of event regarding the gradient magnetic fields and the RF pulses and echo signals is referred to as a pulse sequence. 312 is a bed for object 301—a supine patient in this example.

An important feature of the preferred embodiments of the present invention is the pulse sequence controlled by unit 311. Furthermore, an MRI measuring method using such a pulse sequence and an MR image processing method are important features of the present invention.

Figure 1:
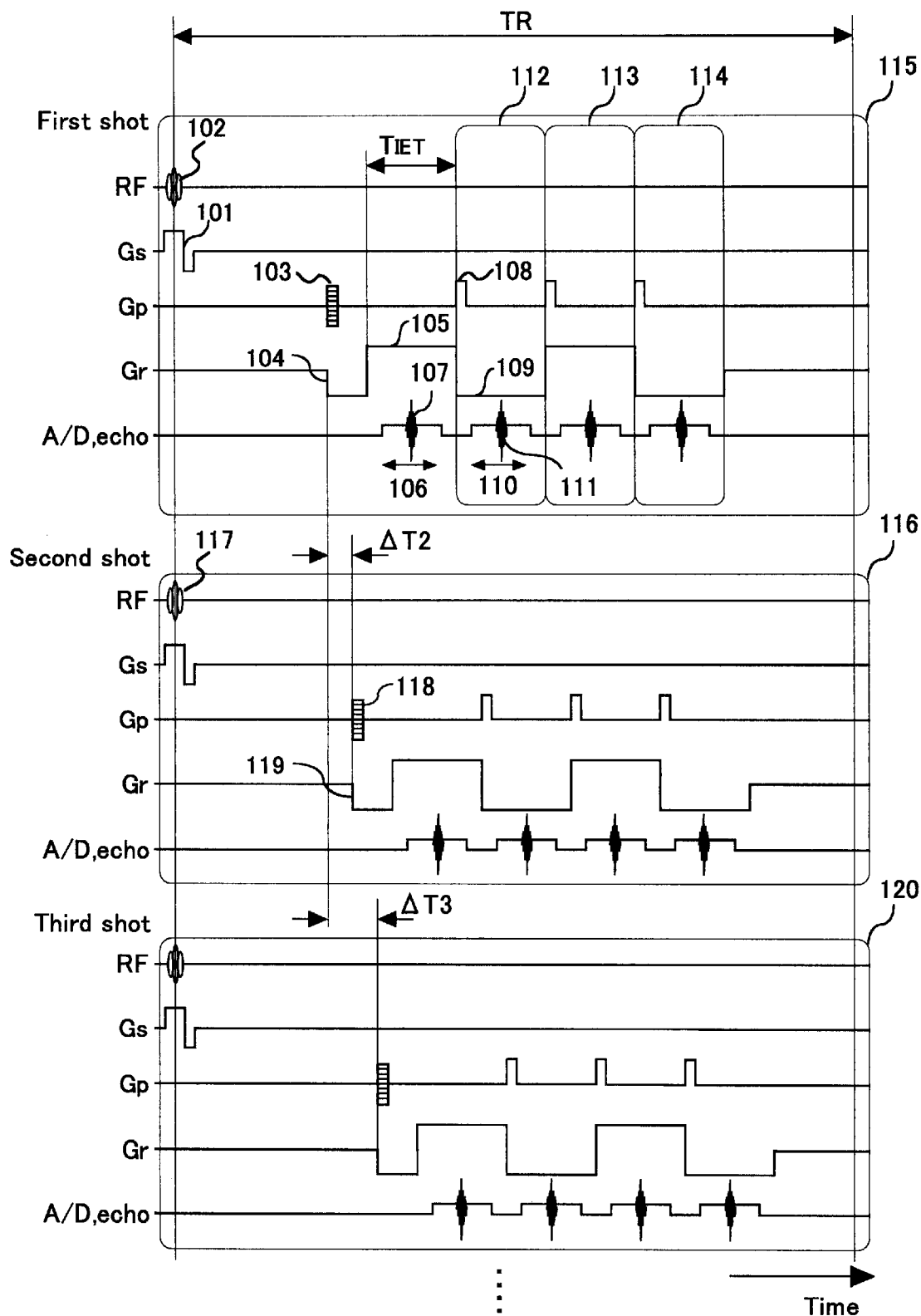
FIG. 1 shows an EPI pulse sequence diagram related to an ETS method.

An EPI sequence using an ETS method is shown in FIG. 1. In FIG. 1, while a slice selection gradient magnetic field pulse (Gs pulse) 101 is applied, spin in a slice in object 301 selected for imaging is excited by applying a radio frequency excitation pulse (RF pulse) 102. Subsequently, phase encoding gradient magnetic field pulses (Gp pulse) 103 and read out direction gradient magnetic field pulses (Gr pulse) 104 are applied, and an echo signal 107 is measured in an A/D period 106 while Gr pulse 105 of a polarity opposite that of Gr pulse 104 is applied.

Subsequently, within a time period 112 a Gp blip pulse 108 is applied concurrently with a Gr pulse 109 and an echo signal 111 is measured in A/D period 110. The process described for time period 112 is repeated in time periods 112, 113, 114, . . . within a repetition time TR. During these repetitions, the polarity of the Gr pulse is reversed alternately. The echo signals acquired in period TR are referred to as an echo train that contains a certain number of echo signals or has a certain length (Echo Train Length: ETL), and the number of an echo signal within the echo train in a TR is referred to as the echo number. FIG. 1 illustrates only 4 echo signals in the train, i.e., a case of 4 ETL, but the number can be a larger integer N, in which case the process of time period 112 is repeated (N−1) times for an N ETL. This process occurring in time period TR is referred to as a shot. The complete process from the start to the end of the shot is identified by the reference numeral 115 in FIG. 1.

Process 116 also is carried out within repetition time TR, as was process 115, but in process 116 the time from RF pulse 117 to Gp pulse 118 and Gr pulse 119 is changed by ΔT2 relative to process 115. The Gp blip pulses that follow pulse 118 also are time shifted by the same delay relative to process 115. By this method, all echo generating times are delayed by ΔT2 in process 116 relative to process 115, and the A/D times are similarly delayed.

The delay time ΔTi pertaining to a shot number i is relevant to filling in data in measuring space (k space), as described later. A further plurality of shots is performed in successive TR intervals, i.e., shots 120, . . . , and all data required to reconstruct an MR image is acquired. The number of TR repetitions is the number of shots.

Figure 2:
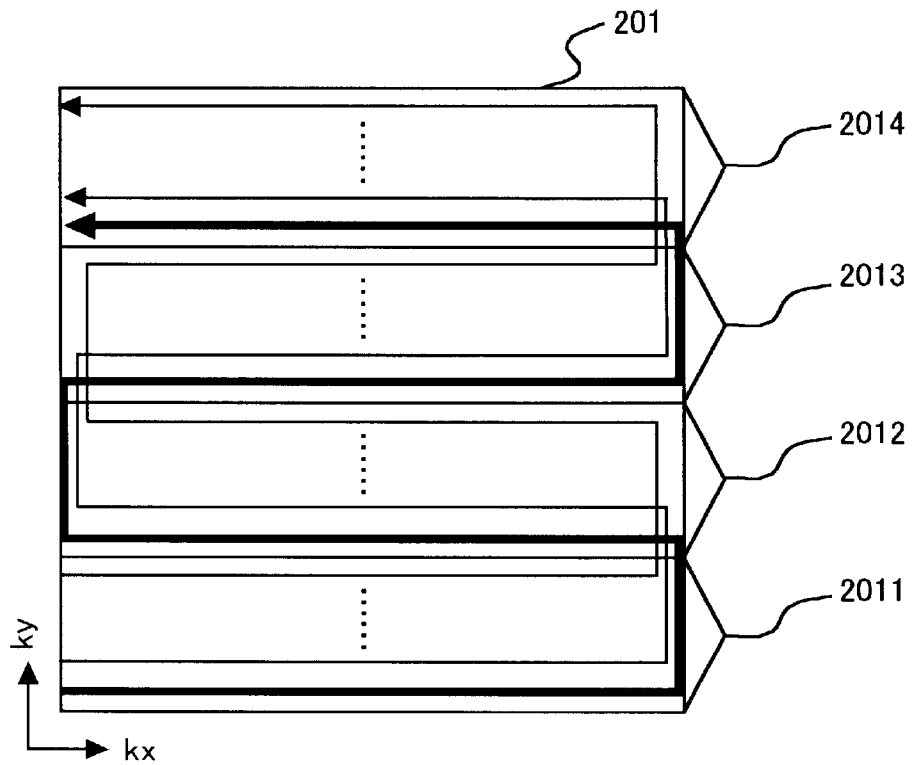
FIG. 2 shows a drawing useful for explanation of k-space filling techniques for data measured by an EPI method.
Figure 2:
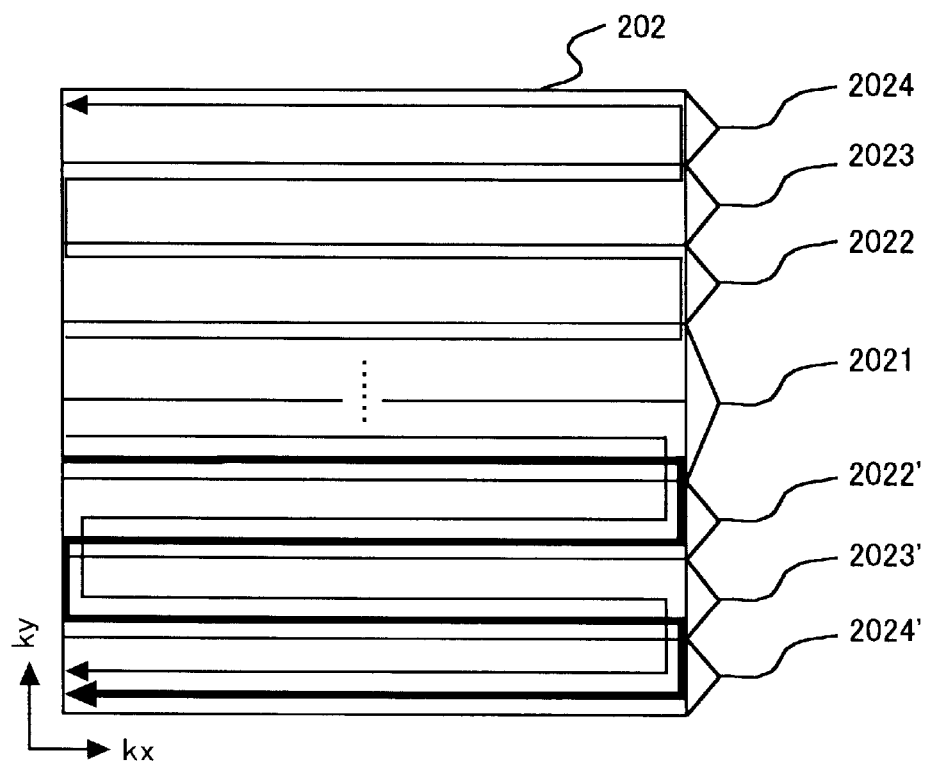

In an EPI method echo signals are acquired to fill k-space, which is memory space storing measurement data in 2 dimensional space with phase direction ky and readout direction kx according to alternating polarity readout direction gradient magnetic fields. The signal acquisition order in time and the data filling order in the k-space depend on the way phase encode gradient magnetic fields are applied. A representative filling procedure is shown in FIG. 2. The arrows in FIG. 2 show the order in which k-space is filled with measurement data. One arrow corresponds to one shot. As shown in FIG. 2, k-space contains portions for data from respective echo signals—a portion for acquiring the first echo, a portion for acquiring the second echo, . . . . Rectangle 201 illustrates a method for filling-up k-space with echo signals from one end to the other of k-space in the ky direction. Rectangle 202 illustrates a method for filling-up k-space from the center to both ends in the ky direction (both up and down). The method illustrated at 201 is referred to as the sequential method and the method illustrated at 202 is referred to as the centric method. FIG. 2 shows an example where ETL is 4. In each of 201 and 202, 2011 and 2021 are portions filled with the first echo signal, 2012 and 2022 and 2022' are portions filled with the second echo signal, 2013 and 2023 and 2023' are portions filled with the third echo signal, and 2014 and 2024 and 2024' are portions filled with the fourth echo signal.

In each of cases 201 and 202, if the time interval of an echo signal is T IET and the total number of shots is N shots, an increment Δt of shift time for a shot interval is T IET/N shot in the sequential method, and is 2T IET/N shot in the centric method. Accordingly, for shot number i, for example, in the case of the sequential method the increment is ΔTi=t×(i−1),and in the case of the centric method if 1≦i≦N shot /2 then ΔTi=Δt(N shot /2−i), and if N shot /2+1≦i≦N shot then ΔTi=t×(i−N shot/2−1).

Figure 4:
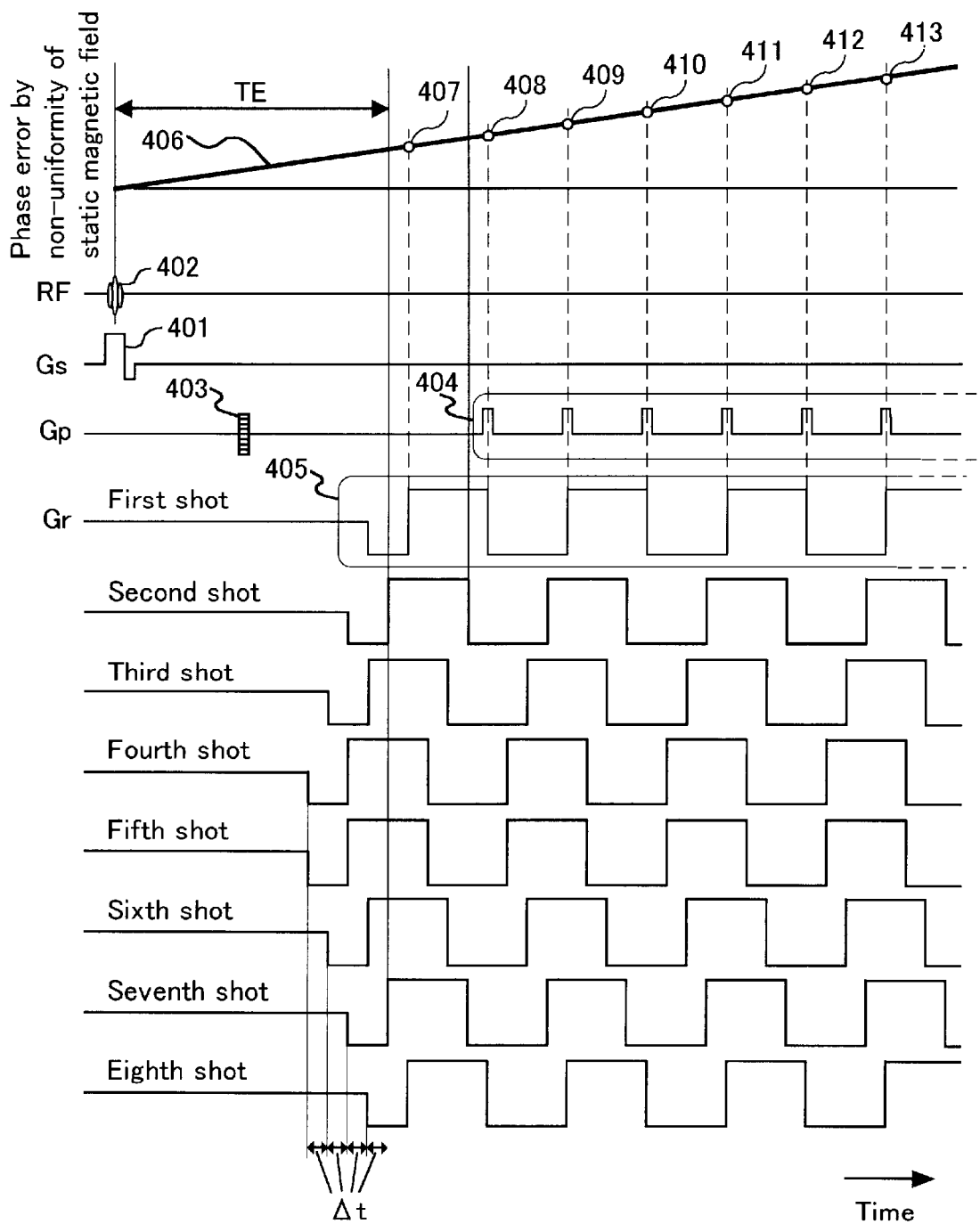
FIG. 4 shows an EPI pulse sequence diagram with an ETS method, in case of a centric 8-echo train.
Figure 5:
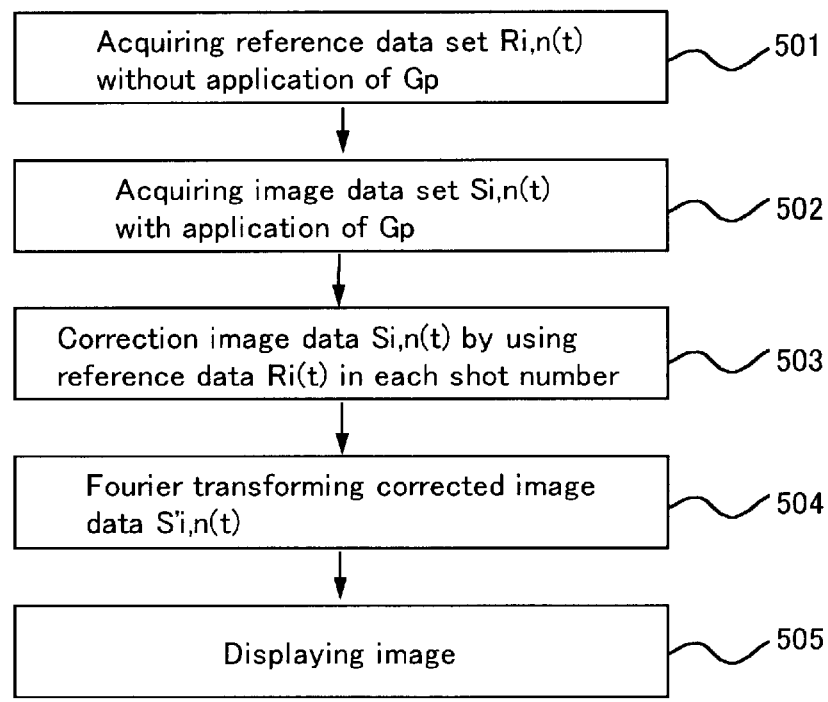
FIG. 5 shows an algorithm used when phase correction is used together with an ETS method.

FIG. 4 shows an EPI pulse sequence with an ETS method for the centric method of 202. FIG. 4 shows the case of 8 shots, so Δt=T IET/4 based on the description above. Accordingly, in this example ΔT1=3 Δt, ΔT2=2 Δt, ΔT3=Δt, ΔT4=0, ΔT5=0, ΔT6=Δt, ΔT7=2 Δt, and ΔT8=3 Δt. After the Gs pulse 401, RF pulse 402 and Gp pulse 403, echo signals are acquired by repeating a plurality of shots with changing the time interval from applying the RF pulse 402 to the start of the Gp blips 404 and the start of the Gr pulses 405 by ΔTi for every shot. Only Gr pulse 405 is numbered in the figure; the Gp pulse 403 is used in appropriate synchronization with the Gr pulse 405 in the first shot and with the Gr pulses in the other shots. Next, it is described when a phase correction method is used together with an ETS method. Acquisition of data for this case and a flow chart of a process are shown in FIG. 5. When imaging using a sequence such as in FIG. 4, at first Gp pulse 403 and pulses 404 are set to zero, and a reference data set Ri,n(t) is acquired. Here i is the shot number, and n is an echo number. This process is carried out at step 501. Next, an image data set Si,n(t) is acquired by application of Gp pulse 403 and pulses 404 as in normal imaging. This process is carried out at step 502. Then, a process is carried out at step 503 that corrects the image data set Si, n (t) by using the reference data set Ri,n (t) acquired in step 501. Thereafter, Fourier transformation is performed at step 504 on the set of correction image data resulting from step 503, and an image based on the resulting data is displayed at step 505.

Figure 6:
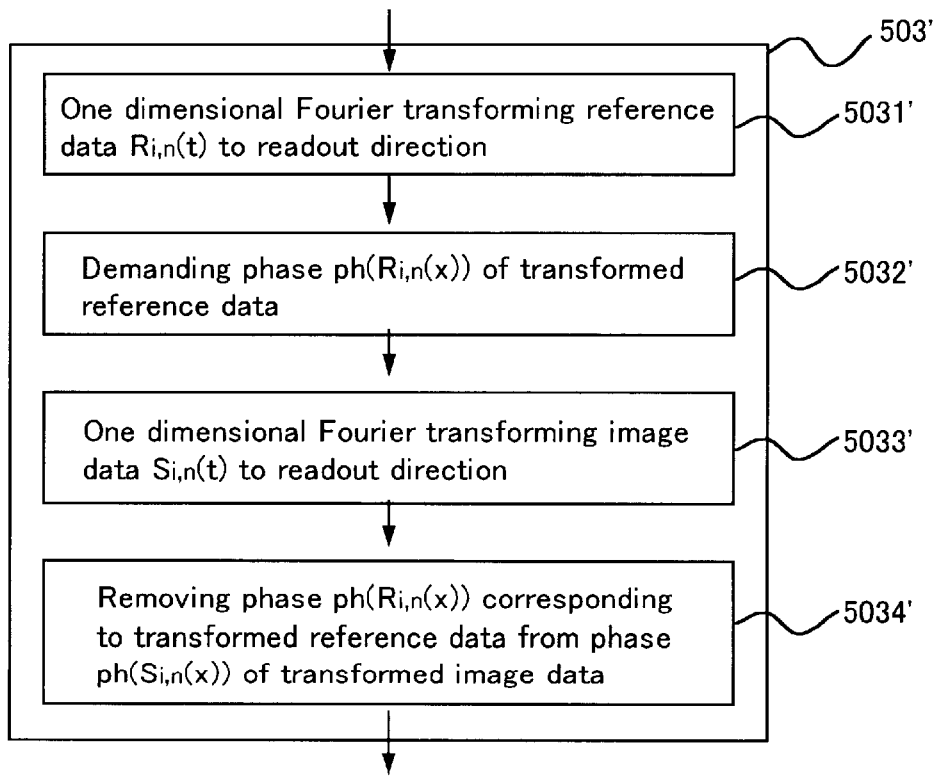
FIG. 6 shows one embodiment of process step 503.

Various algorithms can be considered for carrying out the correction process of step 503. FIG. 6 is one example. In this example, a correction algorithm at step 5031 applies a one-dimensional Fourier transformation to the reference data set Ri,n(t) in the read out direction to produce transformed reference data F{Ri,n(t)}=Ri,n(x). Process step 5032 derives the phase ph(Ri,n(x)) of the result of step 5031. Step 5033 carries out a one-dimensional Fourier transformation on the image data set in the readout direction to produce transformed image data F{Si,n(t)}=Si,n(x) , and process step 5034 removes the phase ph(Ri,n(x)) of transformed reference data Ri,n(x) from the phase of the transformed image data F{Si,n(t)}. Here the expression ph (A) refers to the phase of data A. The order of carrying out process steps 5031, 5032, and 5033 can be reversed.

In the example shown in FIG. 6, the data acquisition time is theoretically double the time for acquiring only a set of image data, as the set of reference data acquired with process 501 is the same size as the set of image data acquired in step 502.

Next, a phase correction algorithm is described using reference data acquired with only one shot. A phase error due to non-uniformity of the static magnetic field increases with time from application of RF pulse 402, as shown at 406 of FIG. 4. The values between actual measurements can be estimated by measuring dispersed phase. For example, reference data R1,n(t) for one shot is acquired with the same timing as the first shot for imaging data by setting to zero pulses 403 and 404. Here subscript 1 means that reference data was acquired with the same timing as the first shot of image data. Then, phase data including phase error components is acquired at times such as 407, 408, . . . 413 ,in the order of echo number n. Phase values between actually measured data are derived by estimating slope, as in line 406.

Figure 7:
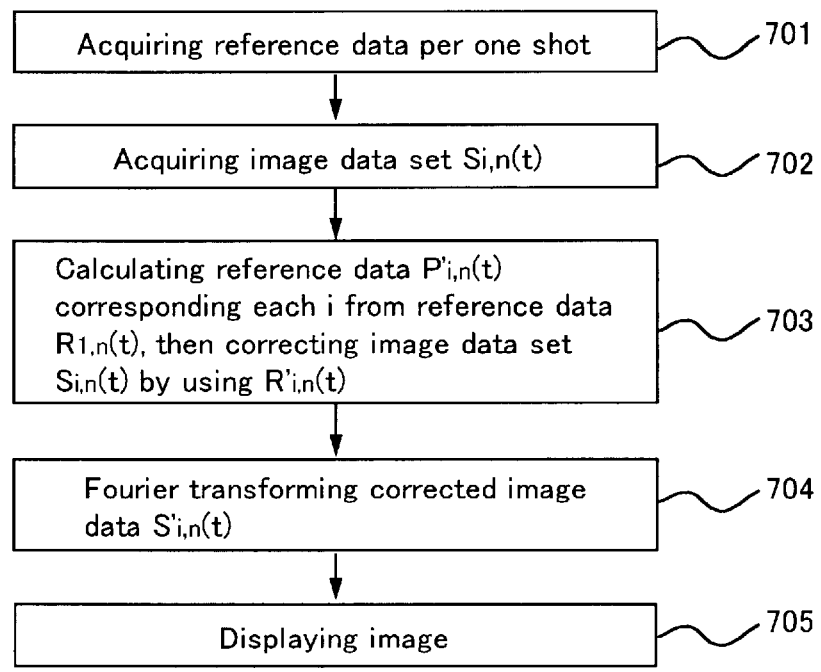
FIG. 7 shows an algorithm used when phase correction is done only with reference data from one shot.

FIG. 7 shows a phase correction algorithm when reference data is acquired with only one shot. As in the example shown in FIG. 5, this correction algorithm has a process step 701 to acquire reference data set R1, n (t), process step 702 to acquire image data set Si,n(t), process step 703 to correct the image data set Si,n(t)by using reference data R1,n(t), process step 705 to perform Fourier transformation on the corrected image data, and process step 705 to display an image. However, in this example the reference data used for correction comes from only one shot. This is the main difference from the example shown in FIG. 5. While only reference data R1,n(t) in shot number 1 can be used for correction, as in this example, it is possible to use reference data from more than one shot. If so, time delays ΔTi should be considered.

Figure 8:
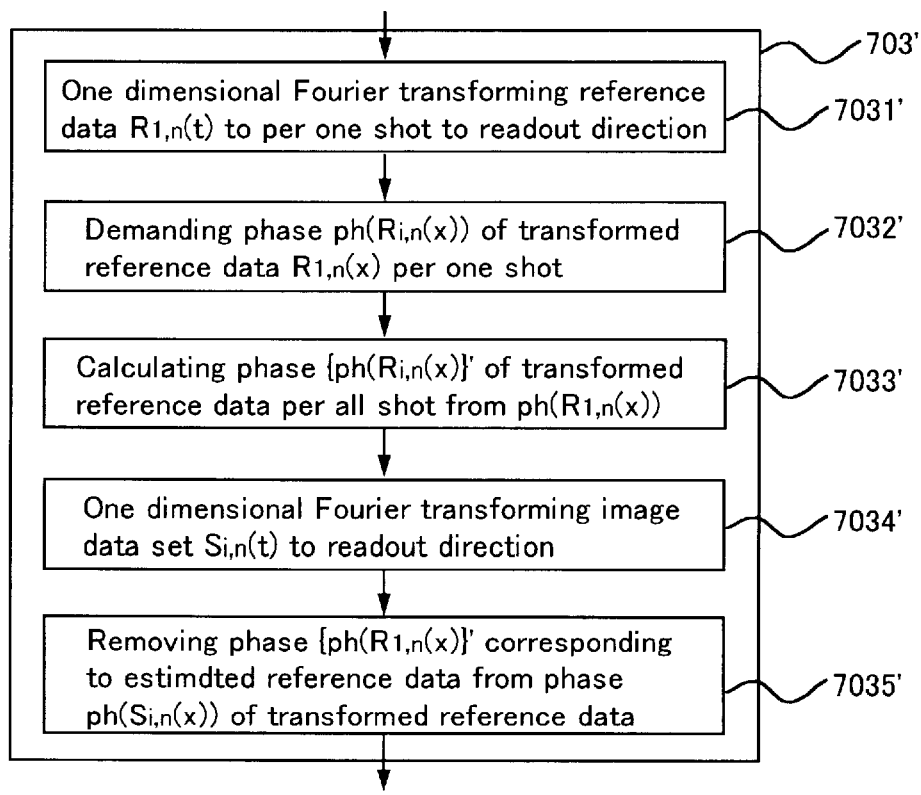
FIG. 8 shows one embodiment of process step 703.

FIG. 8 shows an embodiment of process step 703 to correct image data. This correction procedure uses process step 7031' to perform one-dimensional Fourier transformation in the readout direction on the reference data R1, n (t) acquired in one shot. Process step 7032' derives phase data ph (R1,n (x)) from the Fourier transformed reference data F{R1,n(t)}=R1,n(x), process step 7033' estimates phase data {ph (Ri,n(x))}' of reference data for other shots from the phase ph(R1,n(x)) of the transformed reference data ((R1,n (x)) (the notation ({}') is used to indicate estimated rather than actually measured values), process step 7034' performs one-dimensional Fourier transformation on image data set Si,n(t) in the readout direction, and process step 7035' removes the phase {ph(Ri,n(x)} corresponding to the actual and estimated reference data from the phase ph(Si,n(x)) of the transformed image data F{Si,n(t)}=Si,n(x). The order of process steps 7031' to 7034' can be reversed.

Figure 9:
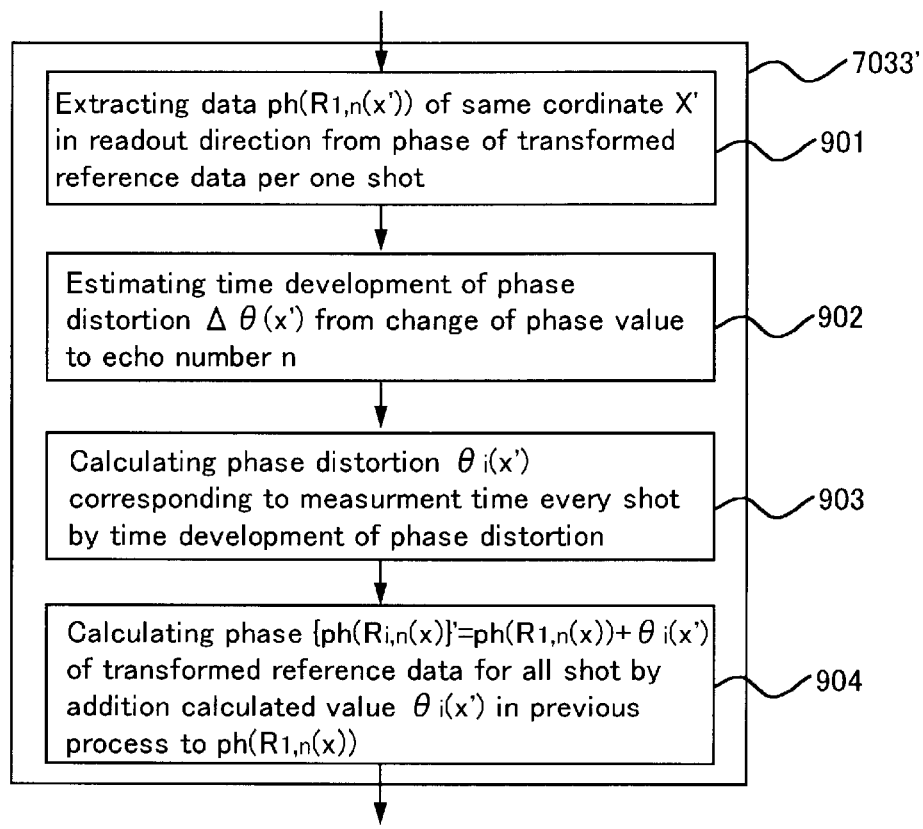
FIG. 9 shows one embodiment of process step 7033'.

FIG. 9 shows an embodiment of a process for estimating the phase {ph(Ri,n(x)) of reference data for all shots, as earlier discussed for process step 7033'. This estimation method uses process step 901 to extract phase values ph(R1, n(x')) from phase values ph(R1,n(x)) of the Fourier transformed reference data from one shot in a coordinate x' (for example, center in the readout direction), process step 902 estimates time development Δθ (x) of phase distortion for change of phase to another echo number, process 903 to calculate phase distortion θi(x') corresponding to measuring time in each shot from a time development of phase distortion, process step 904 calculate phase {ph(Ri,n(x'))}'= ph(R1,n(x))+θi(x') of Fourier-transformed reference data about all shots by adding the phase distortion value calculated in step 903 for one shot. In process steps 901,902, and 903, the estimation of Δθ(x') and calculation of θi(x') may be performed about all x and x' values, or in said estimation and calculation Δθ(x'), θi(x') may be derived for only specific x' and x values.

For example, in the case of a centric process, if 1≦i≦N shot/2 then θi(x')=-(x')/(N shot/2)×(i-1), and if N shot/2+ 1≦i≦N shot then θi(x')=-Δθ(x')/(N shot/2)×(N shot/2-i).

Figure 10:
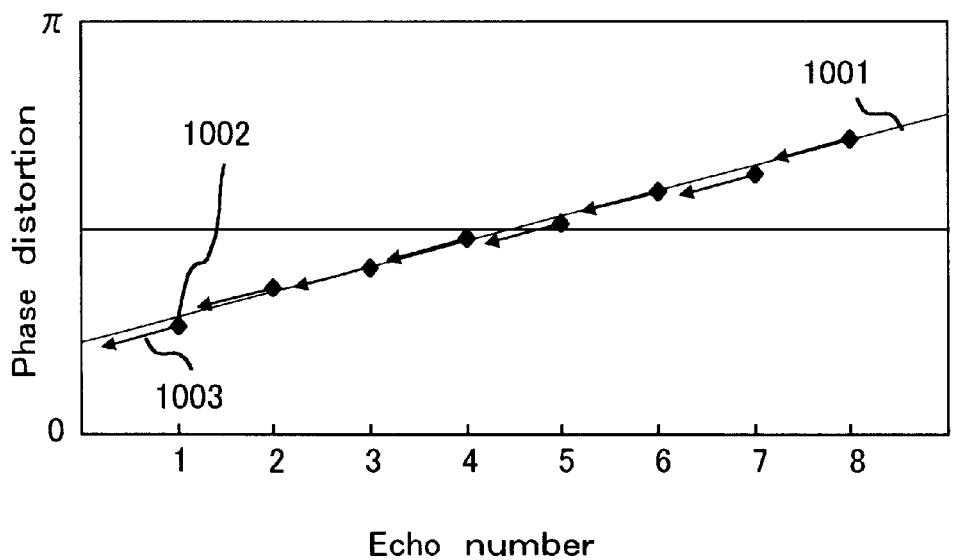
FIG. 10 illustrate graphically one embodiment of process step 902.
Figure 11:
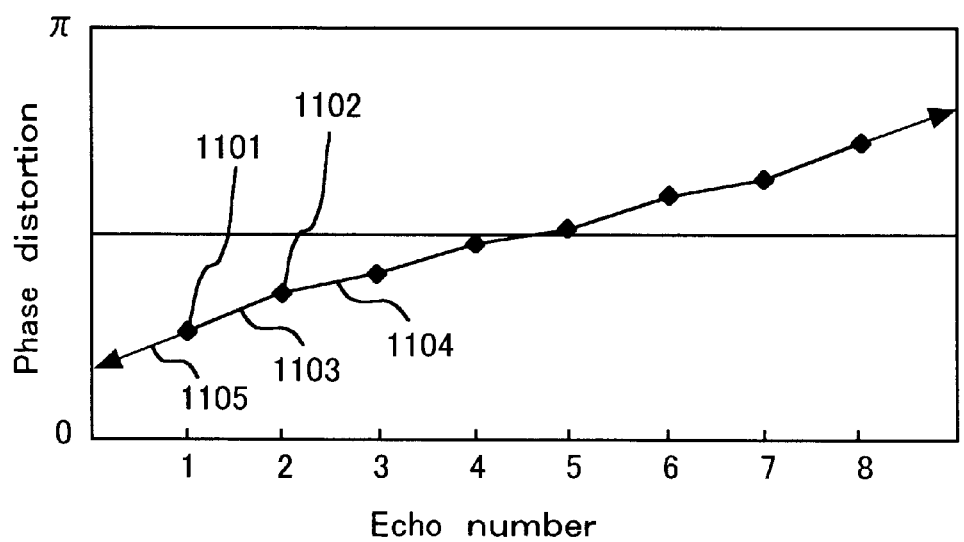
FIG. 11 illustrates graphically another embodiment of process step 902.

An example of a method for estimating time development of phase distortion with process 902 is illustrated graphically in FIGS. 10 and 11.

In FIG. 10 the horizontal axis is echo number and the vertical axis is phase distortion value. The method involves estimating time development of phase distortion by approximating linearly plotted points to each x or x' by using a least squares method for echo number 1 to 8, such as 1001.

1001 has gradient or slope Δθ(x), and expresses time development of phase distortion. After phase distortion θi(x) corresponding to measuring time of each shot is calculated from this value, interpolation to a data point interval is performed with gradient 1003, in the same manner as for 1001, by setting up as starting point the first echo phase 1002. Interpolation to other echo number is done the same way to a data point interval. This method achieves a higher artifact reduction effect than the method shown in FIG. 11.

FIG. 11 shows a method for estimating time development Δθ(x)=Δθn(x) of phase distortion that can be different for each echo number by performing interpolation (or, extrapolation) on the basis of plotted point intervals. For example, phase distortion θi,n(x) corresponding to measurement time for each shot is calculated as the gradient of line 1103 that connects point 1101 of the first echo and point 1102 of the second echo (Δθ2(x)), and the gradient of line 1104 connecting point 1102 of the second echo and the point of the third echo. The same is done with lines connection other data points. Outer portions extending beyond the data points are derived by extrapolation about point 1101 and point 1102, such as at 1105, for example. That is, Δθ1(x)= Δθ2(x). This method involves a reduced amount of calculations in comparison with the method shown in FIG. 10.

The disclosure above illustrates using GrE (Gradient echo) type EPI method but SE (Spin echo) type EPI method also can be used effectively. In addition, for example, hybrid burst method sequences, GRSE (Gradient & Spin echo) method sequences, IR-EPI method sequences, Dynamic EPI method sequences and others can be combined with an ETS method and a phase correction in a manner similar to that disclosed above.

In accordance with the disclosed invention, image quality can be improved to a greater extent that if the ETS method or the phase correction method is used independently. In addition, if the method of acquiring reference data for use in phase correction with only with one shot is used, the resulting increase in overall imaging time is small in comparison to the case of acquiring only image data and, as a result, the time efficiency of imaging is not significantly affected.

What is claimed is:

1. Magnetic resonance imaging method comprising;
   (a) applying slice selecting gradient magnetic fields and radio frequency excitation pulses to an object to be examined;
   (b) applying a series of readout gradient magnetic fields of alternating polarity to the object;
   (c) acquiring reference data by detecting a series of reference signals in the presence of said readout gradient magnetic fields but substantially in the absence of phase encoding gradient magnetic fields;
   (d) acquiring image data for reconstructing an MR image by performing a plurality of shots of said steps (a) and (b) and acquiring said image data form a series of echo signals in the presence of said readout gradient magnetic fields and also in the presence of phase encoding gradient magnetic fields, said shots being over time intervals TR, and said series of echo signals occurring at different times for different shots; and
   (e) phase correcting the image data acquired in the presence of phase encoding gradient magnetic fields by using the reference data acquired substantially in the absence of phase encoding gradient magnetic fields.

2. Magnetic resonance imaging method according to claim 1, in which said reference data is acquired in step (c) using the same number of shots as for said image data acquired in step (d).

3. Magnetic resonance imaging method according to claim 2, in which said reference data is acquired in time synchronization with echo signals for acquiring said image data.

4. Magnetic resonance imaging method according to claim 1, in which said reference data acquired in said step (c) is acquired only at times corresponding to a series of echo signals acquired for a single shot for acquiring image data.

5. Magnetic resonance imaging method according to claim 1 to 4, in which said phase correction is performed by correcting the phase of image data that has been subjected to one-dimensional Fourier transformation by phase information derived from reference data that has been subjected to one-dimensional Fourier transformation.

6. Magnetic resonance imaging method according to claim 4, in which said phase correcting includes using both measured reference data and reference data estimated from said measured reference data.

7. Magnetic resonance imaging apparatus comprising,
   means for generating a static magnetic field in a space accommodating an object to be examined;
   means for exciting nuclear spin within a slice of said object by applying slice selection gradient magnetic fields and RF excitation pulses to said object;
   means for acquiring reference data by detecting a series of echo signals generated from said object by repeatedly inverting a polarity of readout magnetic fields substantially in the absence of phase encoding gradient magnetic fields applied to the excited nuclear spin;
   means for acquiring image data for reconstructing an MR image by repeatedly performing plural shots while applying phase encoding gradient magnetic fields, in a time interval TR per shot, by causing echo signals for one shot to appear at times different from those for another shot; and
   means for phase correcting the image data acquired with application of phase encoding gradient magnetic fields by using the reference data acquired substantially in the absence of phase encoding gradient magnetic fields.

8. A magnetic resonance imaging apparatus comprising,
   a magnet generating a static magnetic field in an imaging space;
   gradient magnetic field and RF excitation sources selectively exciting nuclear spin within an object in said imaging space;

a reference data acquisition system detecting reference echo signals generated from said object in response to said static and gradient magnetic fields and RF excitation, said reference echo signals being generated in respective readout time periods and in the presence of readout gradients of alternating polarity but substantially in the absence of phase encoding applied to the excited nuclear spin;

an image data acquisition system acquiring image data for reconstructing an MR image by performing successive shots with phase encoding, in time intervals TR per shot, and causing echo signals for one shot to appear at times different from those for another shot; and a phase correcting system correcting the image data acquired with application of phase encoding by using said reference data acquired substantially in the absence of phase encoding.

9. A magnetic resonance imaging method comprising, generating a static magnetic field in an imaging space;

selectively applying gradient magnetic fields and RF excitation to selectively excite nuclear spin within an object in said imaging space;

acquiring reference data from reference echo signals generated from said object in response to said static and gradient magnetic fields and RF excitation, said reference echo signals being generated in respective readout time periods in the presence of readout gradients of alternating polarity but substantially in the absence of phase encoding applied to the excited nuclear spin;

acquiring image data for reconstructing an MR image by performing plural shots with phase encoding, by measuring echo signals in time intervals TR, and causing the echo signals for one shot to appear at times different from those for other shots;

phase correcting the image data acquired with phase encoding by using said reference data acquired substantially without phase encoding; and using the phase corrected image data to reconstruct an MR image.

10. A method as in claim 9, in which said reference data comprises data actually measured in a number of shots less than the number of shots in which said image data is acquired, and the actually measured reference data is used to estimate reference data for use in said phase correcting together with the actually measured reference data.

11. A method as in claim 9, in which said phase correcting comprises deriving phase data from the reference data and from the image data, and correcting the phase data derived from the image data with phase data derived from the reference data.

12. A method as in claim 11, in which said phase data is derived from Fourier transformed versions of said reference data and image data.

13. A method as in claim 12 in which said Fourier transformed versions result from one-dimensional Fourier transformation.

14. A method as in claim 9 in which said reference data is comprises data actually measured in a single shot and reference data estimated from the actually measured data, said estimated data corresponding to readout times of echo signals for image data in many shots, where the echo signals of image data for one shot are time shifted relative to those for another shot, and where the estimated data is for times corresponding to said time shifted times.

15. A method as in claim 14 in which said estimated data is derived by interpolation or extrapolation from actually measured data.

* * * * *